United States Patent
Watanabe et al.

(10) Patent No.: US 9,012,513 B2
(45) Date of Patent: Apr. 21, 2015

(54) ANTIOXIDANT, ANTIOXIDANT COMPOSITION AND PRODUCTION METHOD THEREFOR

(75) Inventors: Mitsugu Watanabe, Tokyo (JP); Hitoshi Chiba, Hokkaido (JP); Hirotoshi Fuda, Hokkaido (JP); Shigeki Jin, Hokkaido (JP)

(73) Assignees: Watanabe Oyster Laboratory Co., Ltd., Tokyo (JP); National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 13/980,974

(22) PCT Filed: Jan. 26, 2012

(86) PCT No.: PCT/JP2012/000487
§ 371 (c)(1),
(2), (4) Date: Jul. 22, 2013

(87) PCT Pub. No.: WO2012/102044
PCT Pub. Date: Aug. 2, 2012

(65) Prior Publication Data
US 2013/0303629 A1    Nov. 14, 2013

(30) Foreign Application Priority Data
Jan. 28, 2011    (JP) ................... 2011-016354

(51) Int. Cl.
| | |
|---|---|
| C07C 43/23 | (2006.01) |
| A23L 1/30 | (2006.01) |
| A23L 1/303 | (2006.01) |
| A23L 1/304 | (2006.01) |
| A23L 1/305 | (2006.01) |
| C09K 15/08 | (2006.01) |
| C07C 41/34 | (2006.01) |
| A23L 1/327 | (2006.01) |
| A23L 3/3472 | (2006.01) |

(52) U.S. Cl.
CPC . *C07C 43/23* (2013.01); *A23L 1/30* (2013.01); *A23L 1/303* (2013.01); *A23L 1/304* (2013.01); *A23L 1/3051* (2013.01); *C09K 15/08* (2013.01); *C07C 41/34* (2013.01); *A23L 1/327* (2013.01); *A23L 3/3472* (2013.01)

(58) Field of Classification Search
None
See application file for complete search history.

(56) References Cited

U.S. PATENT DOCUMENTS

| | | | |
|---|---|---|---|
| 5,925,382 A | 7/1999 | Nomura et al. | |
| 2007/0020346 A1* | 1/2007 | Xing et al. | ..... 424/725 |

FOREIGN PATENT DOCUMENTS

| | | |
|---|---|---|
| JP | 10-36275 | 2/1998 |
| JP | 2010-193756 | 9/2010 |

OTHER PUBLICATIONS

Fang et al. (Chem. Pharm. Bull. 58(9) 1236-1239 (2010).*
Watanabe (Antioxidant Activity of *Crassostrea gigas* Meat Extract in Diabetic Mice, Oyster Research Institute News No. 24, 2009, 31-38).*
International Search Report issued May 22, 2012 in International (PCT) Application No. PCT/JP2012/000487.

* cited by examiner

*Primary Examiner* — Jeffrey S Lundgren
*Assistant Examiner* — William Lee
(74) *Attorney, Agent, or Firm* — Wenderoth, Lind & Ponack, L.L.P.

(57) ABSTRACT

Problem
To provide an antioxidant, an antioxidant composition, and a method for producing the antioxidant and the antioxidant composition, which feature a high content rate and degree of extraction of substances. These substances are taurine, glycogen, protein, so-called blood platelet anticoagulant with zinc, fat-soluble vitamin with a high activation such as vitamin D, and other useful substances. The antioxidant and the antioxidant composition also feature a so-called antioxidative property, which has recently attracted attention.
Solution
The present invention, for example, includes 3,5-dihydroxy-4-methoxybenzyl alcohol.

5 Claims, 16 Drawing Sheets

ANTIOXIDANT ACTIVITY TEST OF EACH EXTRACT
THE FLUORESCENCE INTENSITY OF EACH EXTRACT BY AN ORAC METHOD IS SHOWN. THE LONGER THE PERIOD DURING WHICH THE FLUORESCENCE INTENSITY AT THE START OF MEASUREMENT (0 SECONDS) IS MAINTAINED, THE STRONGER THE ANTIOXIDANT ACTIVITY IS.

DPPP  
non-fluorescent

DPPP oxide(1)  
fluorescent

Reaction scheme of DPPP with hydroperoxide 3,5-dihydroxy-4-methoxybenzyl alcohol (μmol/L)

Fig.14

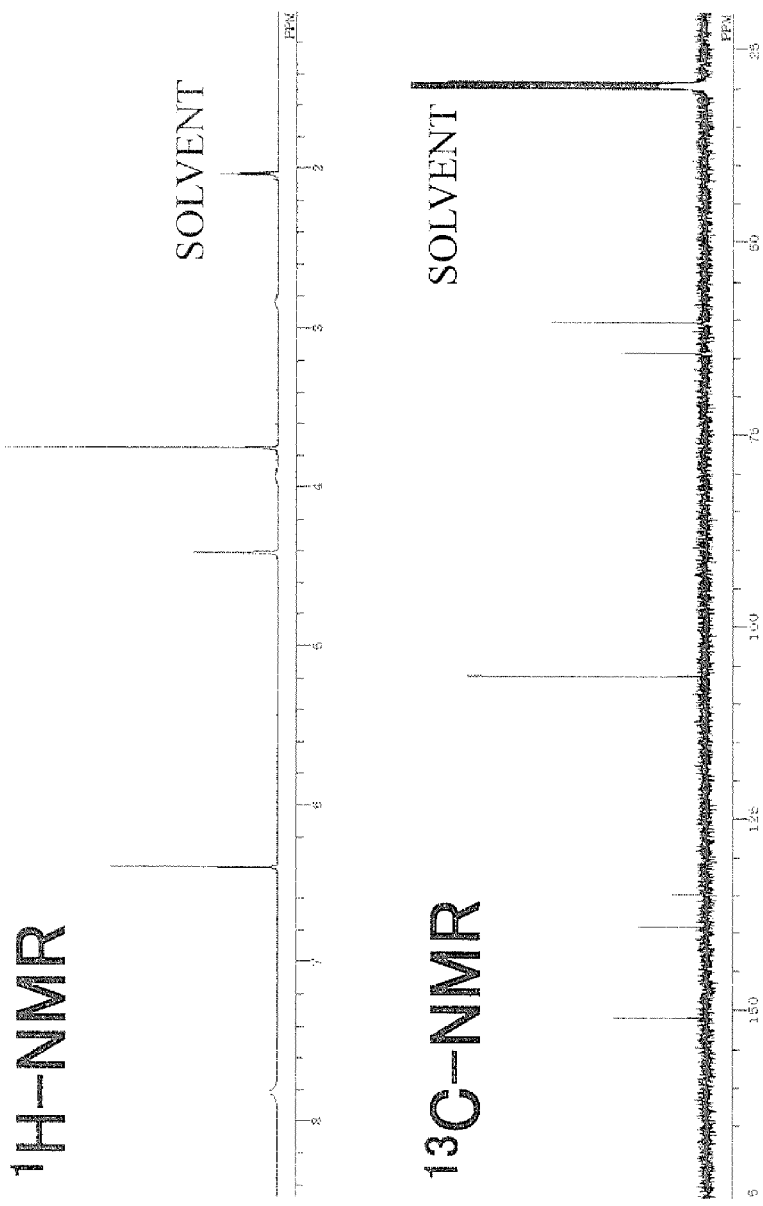

NMR SPECTRUM OF 3, 5-DIHYDROXY-4-METHOXYBENZYL ALCOHOL
IN THE $^1$H-NMR SPECTRUM (TOP), A CHARACTERISTIC SIGNAL DERIVED FROM HYDROXYL WAS OBSERVED AT δ 7.82 AND 3.94 ppm, AND A CHARACTERISTIC SIGNAL DERIVED FROM A METHOXY GROUP WAS OBSERVED AT δ 3.79 ppm. A SIGNAL POSSIBLY DERIVED FROM BENZENE RING WAS OBSERVED AT δ 6.40 ppm. IN THE $^{13}$C-NMR SPECTRUM, FOUR SIGNALS DERIVED FROM BENZENE WERE OBSERVED AT δ 106 to 151 ppm, AND PRESENCE OF A SYMMETRICAL PHENYL GROUP WAS DEMONSTRATED. A METHOXY CARBON SIGNAL AND A METHYLENE CARBON SIGNAL WERE OBSERVED AT δ 60 to 65 ppm.

Fig.15

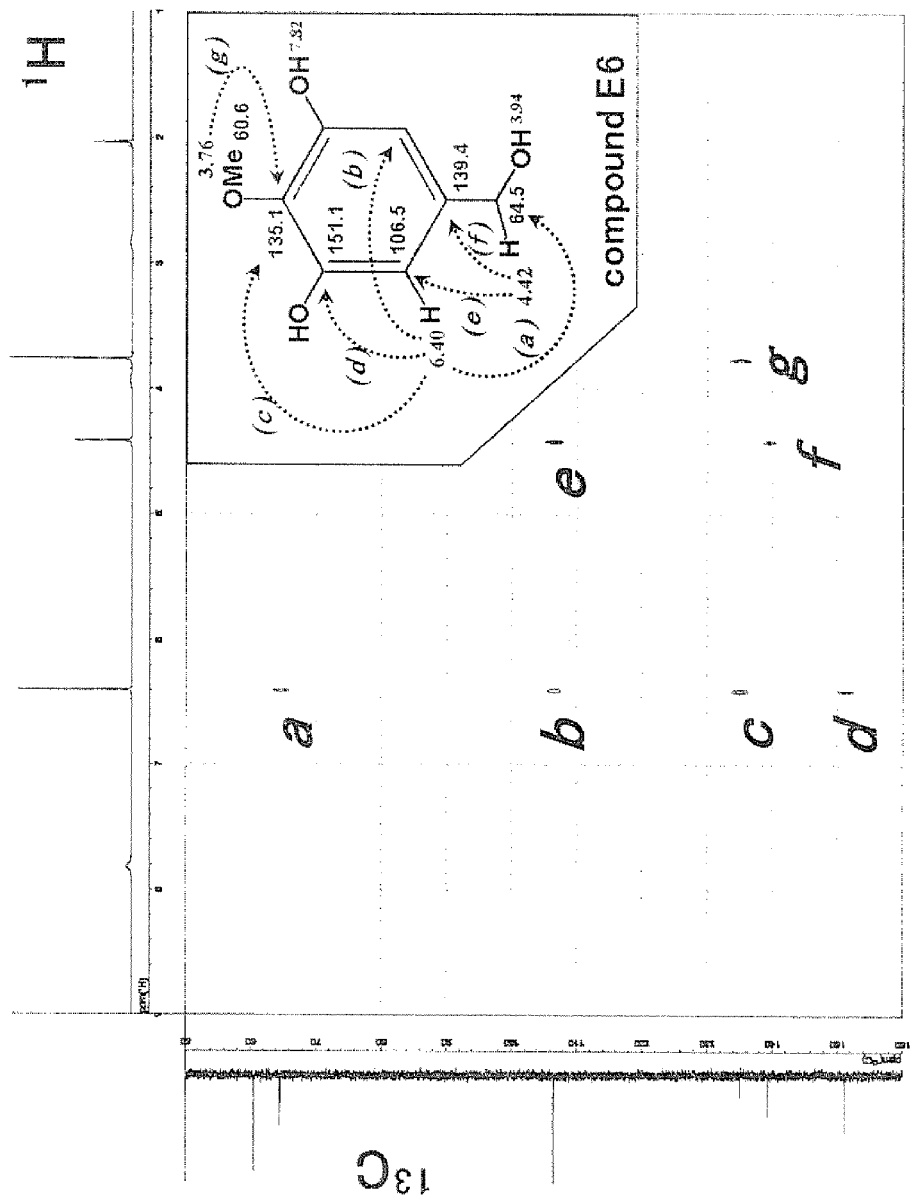

HMBC SPECTRUM (ACETONE-d6) AND PUTATIVE STRUCTURE OF 3,5-DIHYDROXY-4-METHOXYBENZYL ALCOHOL. THE HORIZONTAL AXIS INDICATES 1H-NMR, AND THE VERTICAL AXIS INDICATES 13C-NMR. THE SIGNALS (a) TO (g) INDICATE A CORRELATION FROM A PROTON SIGNAL TO A CARBON SIGNAL IN A LONG RANGE. THE MUTUAL CORRELATION IS ILLUSTRATED IN THE UPPER RIGHT PUTATIVE STRUCTURE. ESPECIALLY, SINCE A CORRELATION SIGNAL FROM METHOXY PROTON TO PHENYL CARBON WAS OBSERVED, DIRECT BINDING OF METHOXY PROTON AND PHENYL CARBON WAS DEMONSTRATED.

ANTIOXIDANT, ANTIOXIDANT COMPOSITION AND PRODUCTION METHOD THEREFOR

TECHNICAL FIELD

The present invention relates to an antioxidant, an antioxidant composition, and a method for producing the antioxidant and the antioxidant composition. Especially, the present invention relates to an antioxidant and an antioxidant composition produced from an oyster meat and a method for producing the antioxidant and the antioxidant composition.

BACKGROUND ART

Conventionally, various methods to extract an extract including various active ingredients from an oyster meat and to produce health food including the active ingredient extract from the oyster meat have been devised. Healthy ingredients including active ingredient extracted from oyster meat are recognized as so-called dietary supplement products. The healthy ingredients attract attention in general as extremely superior product having many beneficial substances. Currently, dietary supplement products regarding a wide variety of active ingredients extracted from oyster meat produced by a wide variety of production methods are sold.

Food products regarding the extract from oyster meat produced as follows are conventionally and generally known. A liquid extract containing the active ingredient extract from oyster meat is, for example, sprayed to a predetermined drum-shaped dehydrated body. The drum-shaped dehydrated body itself is heated for drying. Alternatively, a liquid extract containing the extract from oyster meat is frozen to dehydrate. The extraction and production of the active ingredient extract from oyster meat is, as described above, preferred to be performed as follows. The active ingredient extract from oyster meat can be extracted and produced such that a large amount of sources of nutritional benefit such as glycogen, taurine, protein, or similar material and so-called blood platelet anticoagulant, which contains zinc or similar material, can be contained, and the oyster meat extract can be recovered efficiently.

[Patent document 1] Japanese Unexamined Patent Application Publication No. 2010-193756

DISCLOSURE OF THE INVENTION

Problems to be Solved by the Invention

The present invention is classed as an invention in a series of the above-described conventional original ideas. One of its objectives is to provide an antioxidant from oyster meat extract, an antioxidant composition, and a method for producing the antioxidant and the antioxidant composition. The antioxidant and the antioxidant composition feature high content rate and degree of extraction of substances. These substances contain taurine, glycogen, protein, and so-called blood platelet anticoagulant, which contains zinc, fat-soluble vitamin with high activation such as vitamin D, and other useful substances. The antioxidant and the antioxidant composition also feature a so-called antioxidative property, which has recently attracted attention. For example, the antioxidant and the antioxidant composition generated from an oyster meat and an oyster meat extract containing the antioxidant composition can be efficiently extracted. Accordingly, a large amount of the antioxidant and the antioxidant composition can be extracted from the oyster meat extract and contained for production.

It is generally known that reactive oxygen is generated by aerobic life and causes oxidation of lipid, protein, and nucleic acid, thus damaging a cell. Usually, the oxidation level of a living body is maintained substantially constant by a balance between a reactive oxygen producing system and a scavenging system using an antioxidant substance. The balance is lost due to various factors such as drugs, radiation, ischemia, or similar cause. An inclination to the reactive oxygen producing system is referred to as oxidant stress. It is considered that accumulation of oxidant stress is one cause of various diseases such as cancer, arteriosclerotic disease, an ischemia/reperfusion injury, chronic rheumatoid arthritis, diabetes, a neurological disorder such as an Alzheimer's disease and a Parkinson's disease; and aging.

So-called antioxidant substances are broadly classified into two groups according to constitution. As an enzymatic antioxidant substance, superoxidedismutase (SOD), catalase (CAT), glutathioneperoxidase (GPx), glutathioneS-transferase (GST), glutathionereductase, peroxiredoxin (Prx), and similar material are listed. On the other hand, as a non-enzymatic antioxidant substance, ascorbicacid, α-tocopherol, glutathione (GSH), carotenoids, flavonoids, metallothionein, and similar material are included.

An oyster, for example, Crassostreagigas is a bivalve belonging to a family Ostreidae in the order Pterioida. The habitat covers the entire East Asia region including Japan. Nowadays, a Japanese oyster is also cultivated in France and Australia, and is renowned as the most eaten oyster in the world. Since it is highly nutritious, the oyster has been used for food since ancient times. As described above, it is said that the oyster includes a large amount of minerals such as calcium, zinc, selenium, copper, manganese, or similar material as well as glycogen and protein. As an antioxidant substance derived from the oyster, SOD, CAT, GPx, and Prx6 are reported as an enzymatic antioxidant substance and metallothionein, while uncouplingprotein5 (UCP5), ascorbic acid, α-tocopherol, and β-carotene are reported as a non-enzymatic antioxidant substance.

However, the inventors of the present invention have succeeded to find a so-called novel and excellent antioxidant substance from an oyster. The inventors have also succeeded to determine the chemical constitution and conduct the chemosynthesis of the antioxidant substance. Thus, the inventors have succeeded to provide a so-called novel and excellent antioxidant and antioxidant composition in both cases where the substance is not derived from the oyster and is derived from the oyster. The antioxidant capacity of the substance was also able to be confirmed by an oxidation experiment of human low-density lipoproteins (LDL) and an oxidation experiment of a cell line in a liver.

Means for Solving the Problem

The present invention is characterized as follows. The present invention is an antioxidant including 3,5-dihydroxy-4-methoxybenzyl alcohol. Or, the present invention is an antioxidant composition including 3,5-dihydroxy-4-methoxybenzyl alcohol. Or, the present invention is constituted to include 3,5-dihydroxy-4-methoxybenzyl alcohol contained in a product generated from an oyster meat. Or, the present invention is constituted to include 3,5-dihydroxy-4-methoxybenzyl alcohol contained in an extract extracted from an oyster meat. Or, the present invention recovers a 3,5-dihydroxy-4-methoxybenzyl alcohol fraction from an oyster meat using ethyl acetate. Or, the present invention recovers a 3,5-dihydroxy-4-methoxybenzyl alcohol fraction from an oyster meat using ethyl acetate and ethanol. Or, the present invention stores an oyster meat in an extraction container where an extraction solution is accumulated, collects a solution with an oyster meat extract, adds ethyl acetate to the collected solution with an oyster meat extract, and recovers a 3,5-dihydroxy-4-methoxybenzyl alcohol fraction. Or, the present invention stores an oyster meat in an extraction container where an extraction solution is accumulated, collects a solution with an oyster meat extract, adds ethyl acetate and ethanol to the collected solution with an oyster meat extract, and recovers a 3,5-dihydroxy-4-methoxybenzyl alcohol fraction. Or, the present invention stores an oyster meat in an extraction container where an extraction solution is accumulated, collects a solution with an oyster meat extract, adds ethanol to a collected solution with an oyster meat extract to separate the solution into a supernatant and a precipitate, removes the separated supernatant, adds ethyl acetate to the supernatant to separate the solution into an ethyl acetate layer and a water layer, concentrates a solution of the separated ethyl acetate layer, and recovers a 3,5-dihydroxy-4-methoxybenzyl alcohol fraction.

Advantages of the Invention

With the present invention, an antioxidant and an antioxidant composition including 3,5-dihydroxy-4-methoxybenzyl alcohol derived from an oyster, or not derived from the oyster can be provided. Also, the present invention achieves an excellent effect where a product with an oyster meat extract can be provided. The product with an oyster meat extract includes a comparatively large amount of antioxidant compositions that feature a so-called antioxidative property. Also, the product with the oyster meat extract features high content rate and degree of extraction of substances. These substances include taurine, glycogen, protein, and so-called blood platelet anticoagulant, which contains zinc, fat-soluble vitamin with high activation such as vitamin D, and other useful substances.

BRIEF DESCRIPTION OF DRAWINGS

FIG. 14 is an explanatory view (1) illustrating a structural analysis of 3,5-dihydroxy-4-methoxybenzyl alcohol according to the present invention;

FIG. 15 is an explanatory view (2) illustrating the structural analysis of 3,5-dihydroxy-4-methoxybenzyl alcohol according to the present invention.

BEST MODE FOR CARRYING OUT THE INVENTION

Figure 1:
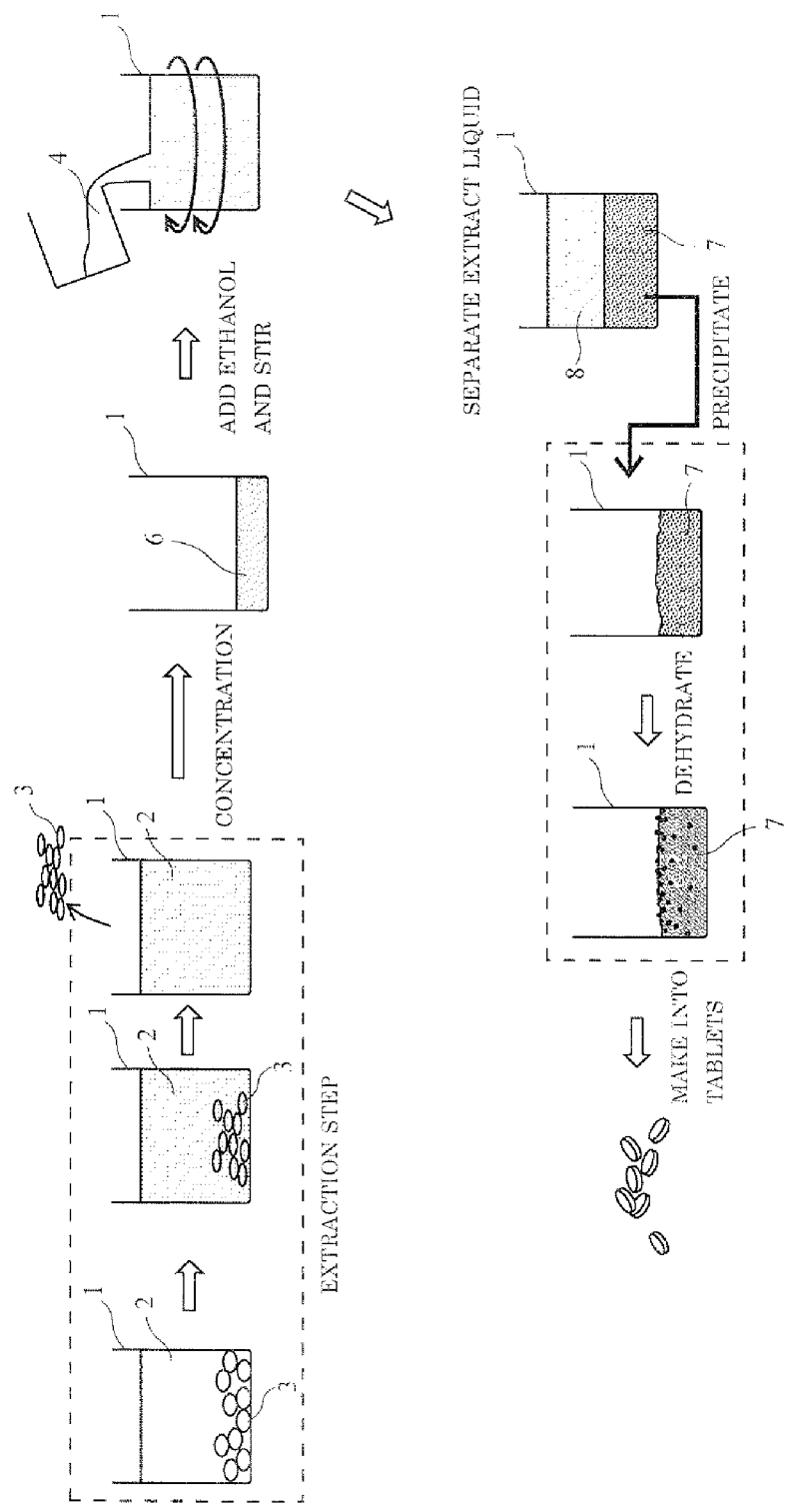
FIG. 1 is a schematic configuration explanatory view (1) illustrating a schematic configuration of the present invention.

The following describes the present invention based on one working example illustrated in the drawings.

WORKING EXAMPLE

Figure 2:
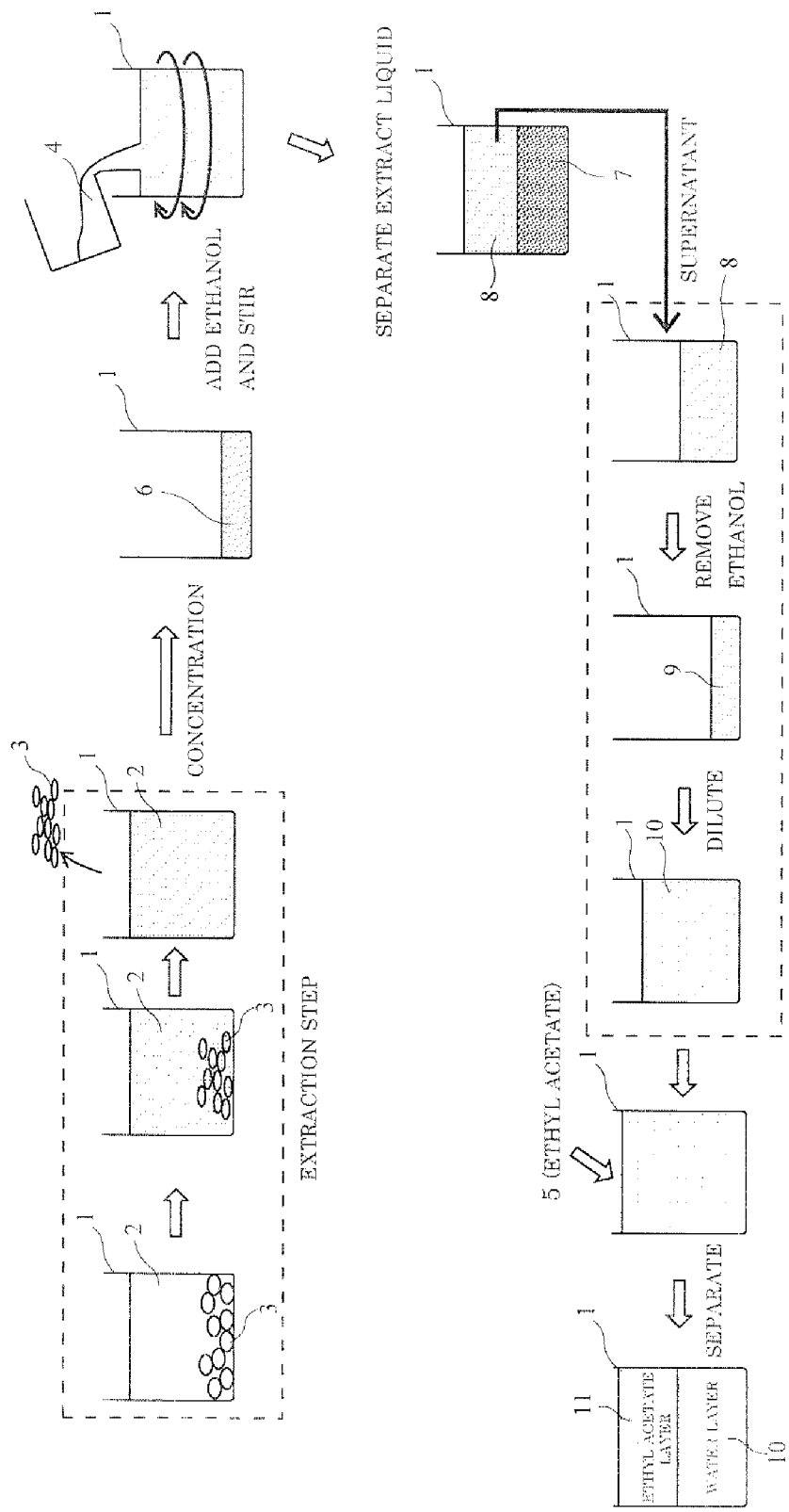
FIG. 2 is a schematic configuration explanatory view (2) illustrating the schematic configuration of the present invention.

In FIG. 1 and FIG. 2, reference numeral 1 denotes an extraction container. The extraction container 1 accumulates an extraction solution 2 to extract an extraction from an oyster meat. Then, raw oyster meat 3 is stored in the extraction container 1 accumulating the extraction solution 2. Thus, the extraction containing various active ingredients of the oyster meat is extracted.

Conventionally, when extracting the oyster meat extract, the extraction solution 2 in the extraction container 1 where the oyster meat 3 is stored may be stirred for further efficient extraction. This damages the oyster meat 3 itself; therefore, it is preferred that a stirring operation be not performed during the extraction step. The extraction solution 2 where the oyster meat extract is extracted as described above is then concentrated in a concentration step.

Next, an ethanol solution 4 is added to a concentrated liquid 6. Thus, a solution with an ethanol concentration approximately 70% is formed. Then, the solution is stirred and separated into a precipitate 7 and a supernatant 8. As seen from FIG. 1, the precipitate 7 is dehydrated, made into tablets, and finally provided to health food or similar product.

Conventionally, it has been regarded that the supernatant 8 did not include any active ingredient of the oyster meat extract or include a trace amount of the oyster meat extract. Therefore, the supernatant 8 was disposed. However, afterwards, according to experiment and study results, it was found that the supernatant 8 included many active ingredients regarding the oyster meat extract. Currently, the supernatant 8 is used without being disposed. Nowadays, the supernatant 8 is concentrated again, and the concentrated liquid is finally dehydrated. The dehydrated material does not become a complete solid material shape but can be formed into a paste shape. Accordingly, the dehydrated material is produced as a paste-type health food or similar product. Then, this paste-type health food is dissolved in hot water or similar liquid by a customer and provided as a health food beverage.

First, this working example recovered the oyster meat extract containing 3,5-dihydroxy-4-methoxybenzyl alcohol, which will be describe later, using the supernatant 8. That is, after dissolving the solution into the precipitate 7 and the supernatant 8 as described above, ethanol was removed from the supernatant 8 by an evaporator or similar apparatus. Then, the supernatant 8 was concentrated until the amount of the supernatant 8 becomes approximately half. For example, the supernatant 8 of 40 mL was concentrated to obtain concentrated liquid 9, which is the supernatant 8 of 20 mL.

Next, the concentrated liquid of 20 mL was diluted so as to be 5 times the concentrated liquid to generate a diluted solution 10. For example, the concentrated liquid of 20 mL became the diluted solution 10 with the amount of 100 mL. This step was performed to remove impurities as much as possible. Then, for example, ethyl acetate 5 of approximately 200 mL was, for example, added into the solution of the diluted solution 10 of 100 mL. Then, the solution was separated into a water layer 10 and an ethyl acetate layer 11 by stirring or similar method or by using a separator. Over time, the mixed solution was separated into the water layer 10 and the ethyl acetate layer 11.

Then, it was confirmed that the ethyl acetate layer 11 included 3,5-dihydroxy-4-methoxybenzyl alcohol, which will be described below. Regarding the amount of the confirmed 3,5-dihydroxy-4-methoxybenzyl alcohol, specifically, it was confirmed that the ethyl acetate layer 11 collected approximately 2 L included 3,5-dihydroxy-4-methoxybenzyl alcohol of approximately 3 mg.

Next, the following will be described: what process separates and purifies the 3,5-dihydroxy-4-methoxybenzyl alcohol from the oyster meat extract, how to confirm the presence of the 3,5-dihydroxy-4-methoxybenzyl alcohol in the oyster meat extract, what constitutes the 3,5-dihydroxy-4-methoxybenzyl alcohol, and how to confirm the antioxidant effect of the 3,5-dihydroxy-4-methoxybenzyl alcohol.

Figure 3:
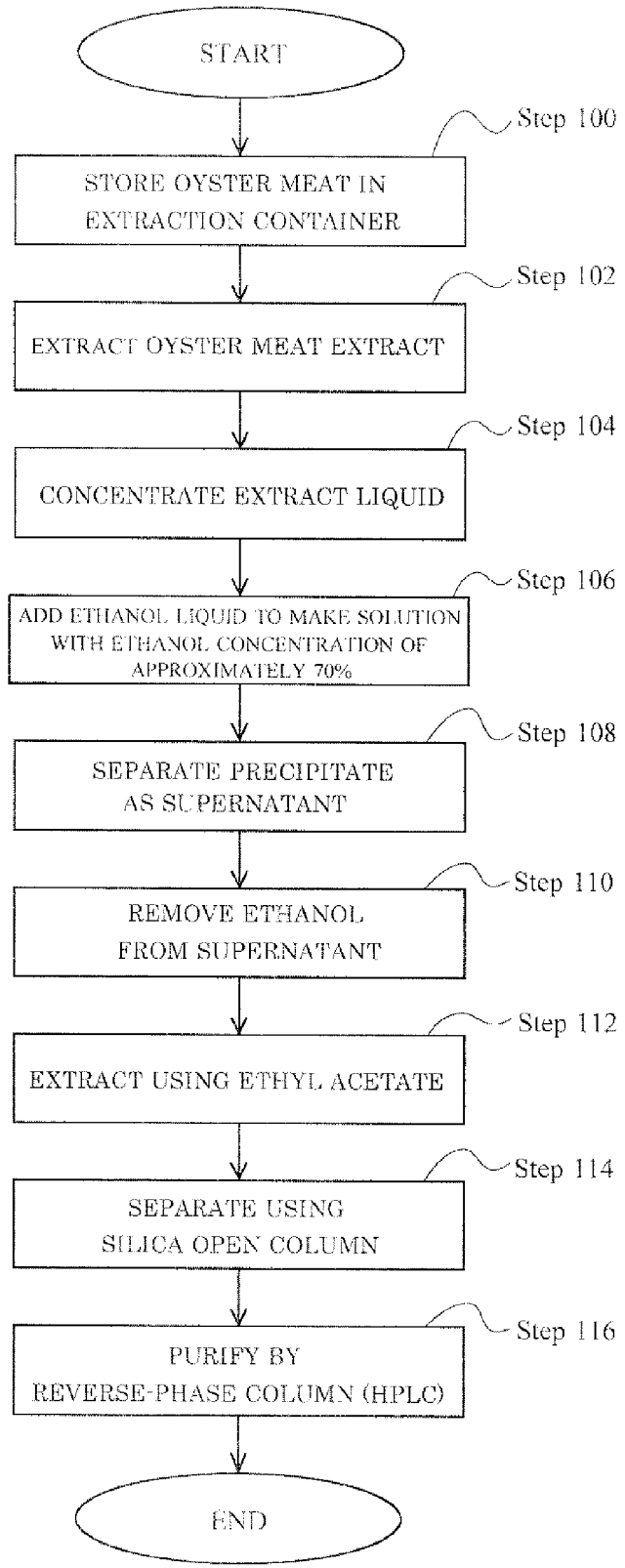
FIG. 3 is an explanatory view illustrating a flowchart of the present invention.

The description will be given with reference to the flowchart illustrated in FIG. 3. For example, the oyster meat 3 was added in the extraction solution 2 containing the ethanol solution 4 to extract an active ingredient extract from oyster meat (Step 100 and Step 102). After extraction, the extract liquid was concentrated (Step 104). Then, for example, the ethanol solution 4 was added to the concentrated liquid 6 to make the concentrated liquid 6 be a solution with an ethanol concentration of approximately 70% (Step 106). Then, the solution was stirred to separate it into the precipitate 7 and the supernatant 8 (Step 108).

Then, using the supernatant 8, an extraction operation using ethyl acetate, which extracts 3,5-dihydroxy-4-methoxybenzyl alcohol, was performed. As seen from FIG. 3, the ethanol was removed (Step 110) and chloroform, ethyl acetate, and butanol were added from the respective hexanes to the supernatant 8 that were diluted approximately five times, so as to generate fractions of the respective substances.

Figure 4:
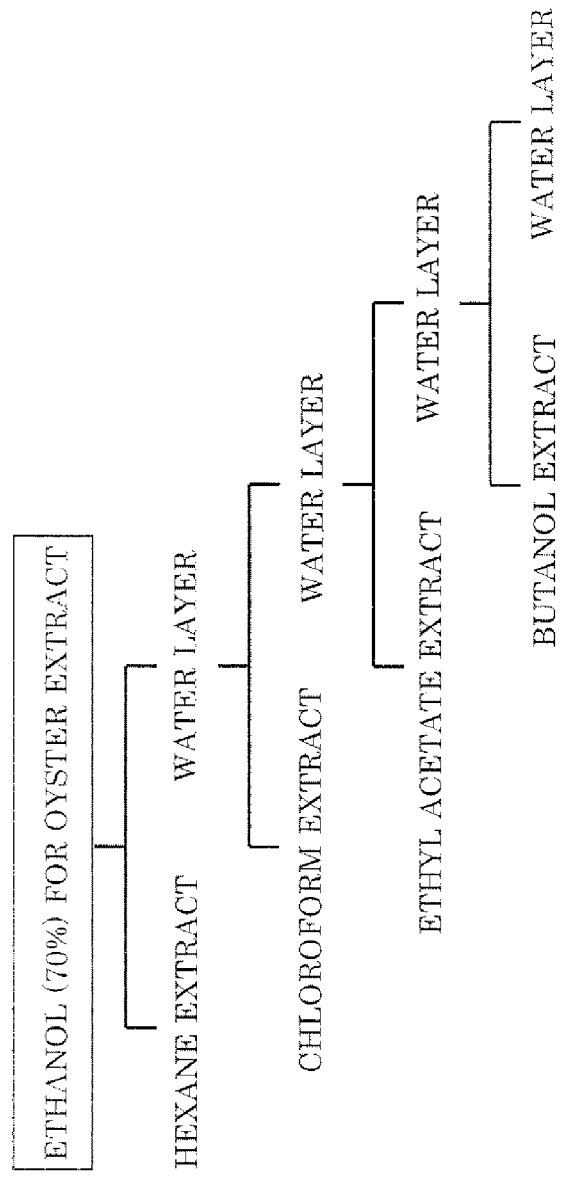
FIG. 4 is an explanatory view illustrating a state where a polarity of an organic solvent is increased in phases to extract 3,5-dihydroxy-4-methoxybenzyl alcohol.

For example, the solution was concentrated up to 100 mL by a rotary evaporator or similar apparatus. For example, a distilled water of 80 mL was added to the concentrated liquid of 20 mL, the solution was transferred to a separation funnel, and hexane extraction was performed. After removal of a hexane layer (200 mL), a chloroform of 200 mL, an ethyl acetate of 200 mL, and a butanol of 200 mL were extracted from the water layer step-by-step in this order. That is, the polarity of the organic solvent to extract 3,5-dihydroxy-4-methoxybenzyl alcohol was increased step-by-step. Fractions where the respective organic solvents were added were generated. Whether the 3,5-dihydroxy-4-methoxybenzyl alcohol was extracted to each of the fractions or not is confirmed (see FIG. 4).

Next, after concentrating the fractions where the respective organic solvents have been added, for example, by an evaporator, the fractions were observed with a Thin-Layer-Chromatography (hereinafter referred to as TLC). Then, antioxidative potency was searched by a so-called OxygenRadicalAbsorbanceCapacity method (ORAC method). As a result, it was confirmed that in the TLC image, the fractions were eluted in order of the fraction with the lower polarity to the fraction with higher polarity, that is, in order of hexane, chloroform, ethyl acetate, and butanol.

Figure 5:
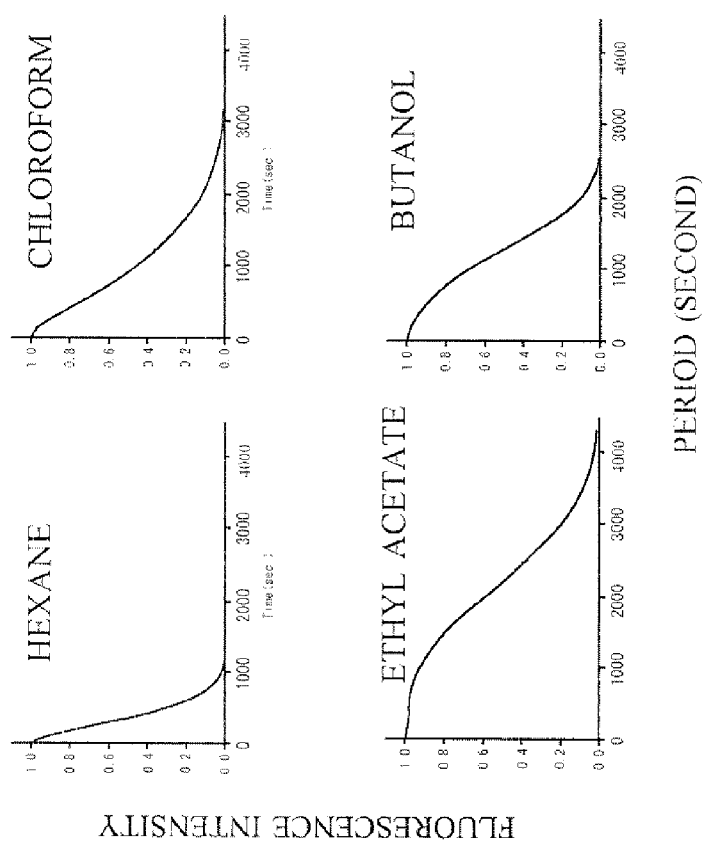
FIG. 5 is an explanatory view illustrating a result of an antioxidant activity test of each extract.

In the ethyl acetate fraction, a plateau portion was observed by the ORAC method, and a high antioxidant capacity was recognized in the ethyl acetate fraction. Accordingly, it was determined that 3,5-dihydroxy-4-methoxybenzyl alcohol existed in the ethyl acetate fraction (see FIG. 5, Step 112).

Figure 6:
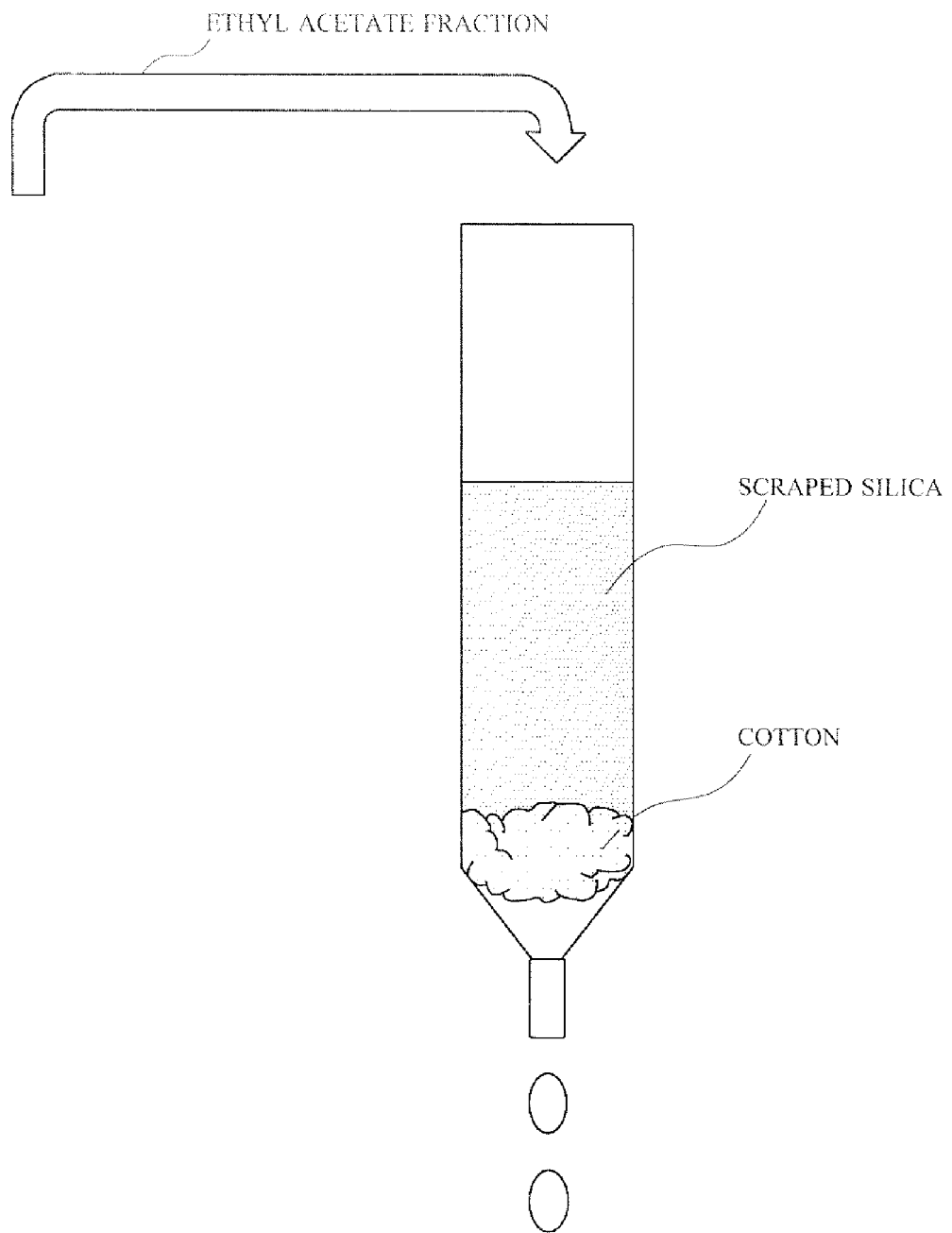
FIG. 6 is an explanatory view illustrating an extract using a silica open column.
Figure 7:
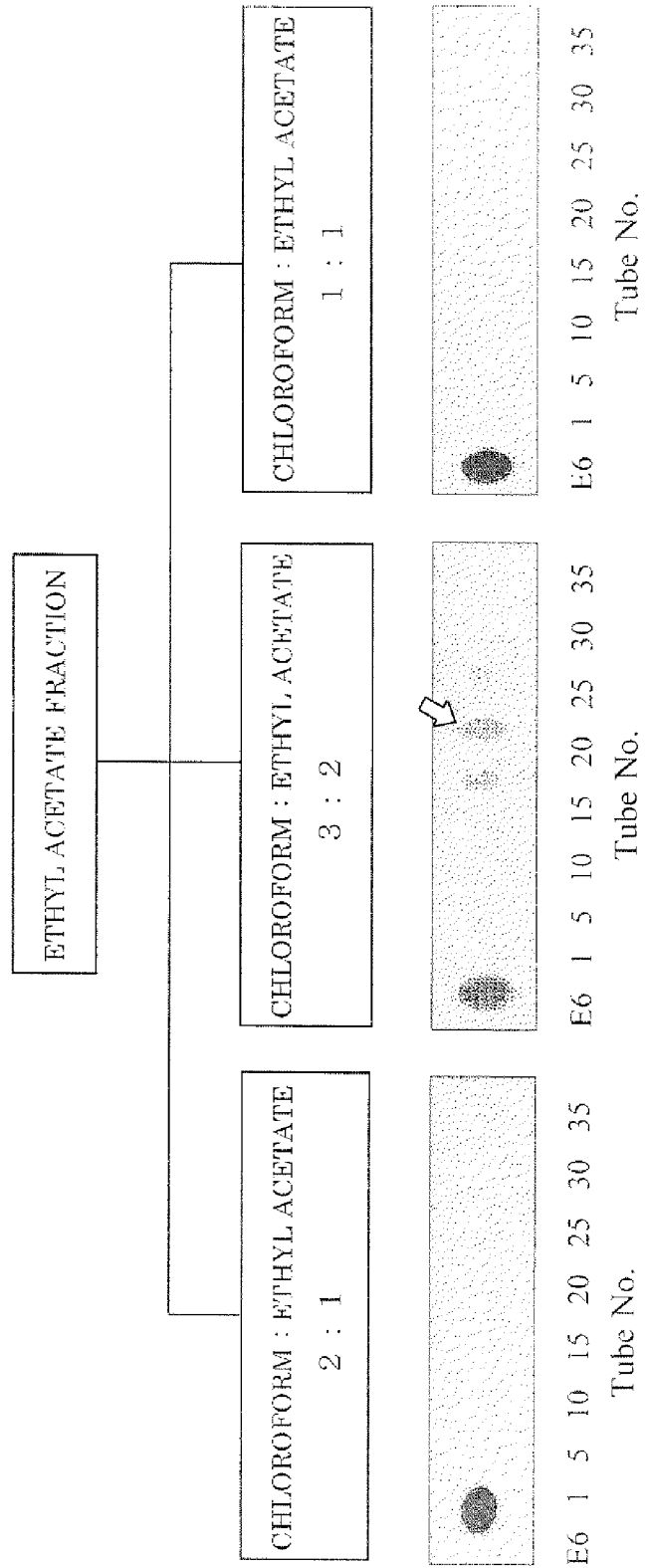
FIG. 7 is an explanatory view illustrating an ethyl acetate fraction extract.

Next, after concentrating the ethyl acetate fraction by the evaporator, extraction using a so-called silica open column was performed (FIG. 6, Step 114). An extraction fraction where the proportion between ethyl acetate and chloroform is 3:2 was selected (see FIG. 7). Finally, 3,5-dihydroxy-4-methoxybenzyl alcohol was able to be separated and purified from the fraction by reverse-phase column (HPLC) (Step 116). Thus, 3,5-dihydroxy-4-methoxybenzyl alcohol was able to be separated and purified from the supernatant 8 where the oyster meat extract has been extracted.

The 3,5-dihydroxy-4-methoxybenzyl alcohol can be separated and purified by the following operation. First, Trolox (Wako) or a test sample of 0.05 mL dissolved in a mixed solution of 0.075 mol/L phosphoric acid buffer solution 2.3 of 5 mL, $6.3 \times 10^{-7}$ mol/L Fluorescein (fluorescent probe) of 0.3 mL, and 7% (w/v) methylated β-cyclodextrin (Wako) was warmed for 10 minutes at 37° C.

$1.28 \times 10^{-1}$ mol/L2,2'-azobis(2-amidinopropane)dihydrochloride (AAPH, Wako), which has been preliminarily warmed at 37° C., was added by 0.3 mL. For example, while stirring with a stirrer, a fluorescence intensity (excitation wavelength: 493 nm, fluorescence wavelength: 515 nm) was measured for every 10 seconds and up to 5,000 seconds by a spectrofluorophotometer (FP-6500, JASCO, Tokyo).

An antioxidant activity is indicated by length of period (for example, the horizontal axis in FIG. 5) during which a measured fluorescence value (the vertical axis in the same drawing) at the start of measurement is maintained. The longer the period, the stronger the antioxidant activity is. The antioxidant activity was confirmed in the ethyl acetate extract fraction among the four kinds of the extract fractions.

Next, a silica gel thin layer fractionation chromatography of normal phase is performed on the ethyl acetate extract showing an antioxidant activity. Using a silica gel thin layer plate (200×200 mm, thickness: 0.5 mm, Merck, Darmstadt), and ethyl acetate-chloroform (2:1, v/v) was used as a mobile phase. An ultraviolet lamp (254 nm) was irradiated to the plate after deployment and 11 fractions with ultraviolet absorption feature were obtained. The sample of each fraction was separated together with a gel carrier. For example, when the antioxidant activity was measured after elution with methanol, the antioxidant activity was observed in the sixth fraction from the low polarity side.

Furthermore, the fraction showing antioxidant activity in the Thin-Layer-Chromatography was purified by a high performance liquid chromatography (HPLC). The fraction was separated at room temperature using a HPLC system (pump: L-2130, UV detector: L-2420, HITACHI, Tokyo), a reverse-phase column (APCELLPACC18, 250×4.6 mm I.D., SHISEIDO, Tokyo), and a mobile phase with acetonitrile solution of 5% (flow rate: 1.0 mL/min). Also this operation finally obtains 3,5-dihydroxy-4-methoxybenzyl alcohol of 3.0 mg from ethanol extract liquid of 160 mL, which is the source material.

The presence of the 3,5-dihydroxy-4-methoxybenzyl alcohol was presumed as follows. An ultraviolet absorption spectrum (V-530, JASCO), a nuclear magnetic resonance spectrum (NMR: AMX-500, Bruker, Karlsruhe), and a mass spectrum (JMS-T100CS, JEOL, Tokyo) were measured, and structural analysis was performed (FIG. 14 and FIG. 15). As a result, the constitution of the substance that was separated and purified was presumed as 3,5-dihydroxy-4-methoxybenzyl alcohol (FIG. 15).

Condition

UV (EtOH), $\lambda_{max}$ 270 nm; $^1$H-NMR (500 MHz, Acetone-$d_6$) $\delta_H$: 7.82 (2H, br.s, aromatic-OH), 6.40 (2H, s, H-2, 6), 4.42 (2H, s, H-1'), 3.94 (1H, br.s, —OH), 3.79 (3H, s, —OMe); $^{13}$C-NMR (125 MHz, Acetone-$d_6$) $\delta_C$: 151.1 (C-3, 5), 139.4 (C-1), 13, 5.1 (C-4), 106.5 (C-2, 6), 64.5 (C-1'), 60.6 (—OMe); ESI-TOFMS, m/z153.05451 [M-OH]$^+$ (calc. for $C_8H_8O_3$, 153.05517), 171.06911 [M+H]$^+$ (calc. for $C_8H_{11}O_4$, 171.06573).

Figure 8:
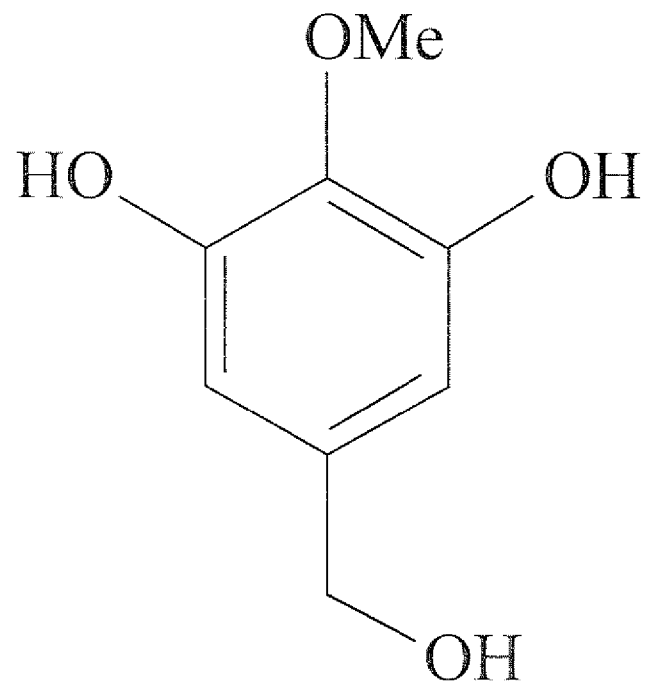
FIG. 8 is an explanatory view illustrating a constitution of 3,5-dihydroxy-4-methoxybenzyl alcohol extracted according to the present invention.

Here, the properties of 3,5-dihydroxy-4-methoxybenzyl alcohol, which was separated and purified, will be described. The properties are pale-yellow powder and show lipid solubility and water solubility. It was confirmed that the 3,5-dihydroxy-4-methoxybenzyl alcohol was a phenolic compound as illustrated in FIG. 8.

Methods for measuring an antioxidant substance in a food product have been variously reported. However, all the methods have a drawback and an advantage, and therefore the method has not been standardized or determined as an official method (confirmation of validity of an analysis value). However, in the United States of America, a supplement and a beverage with an ORAC value have already been on the market. This trend is becoming a world standard. Accordingly, in this working example, the antioxidative potency is measured by the ORAC method.

A research conference that studies on employing the ORAC method as an official method (Antioxidant-Unit Research Association) has already been founded in Japan. The ORAC method has advantages in that both a soluble sample and a liposoluble sample can be measured and the above-described any organic solvent fractions can be measured. One measurement by the ORAC method can evaluate both the duration and the titer of the antioxidant effect, and therefore, for example, an experiment operation is simple. The ORAC method was considered to be advantageous in measurements in this working example.

Figure 9:
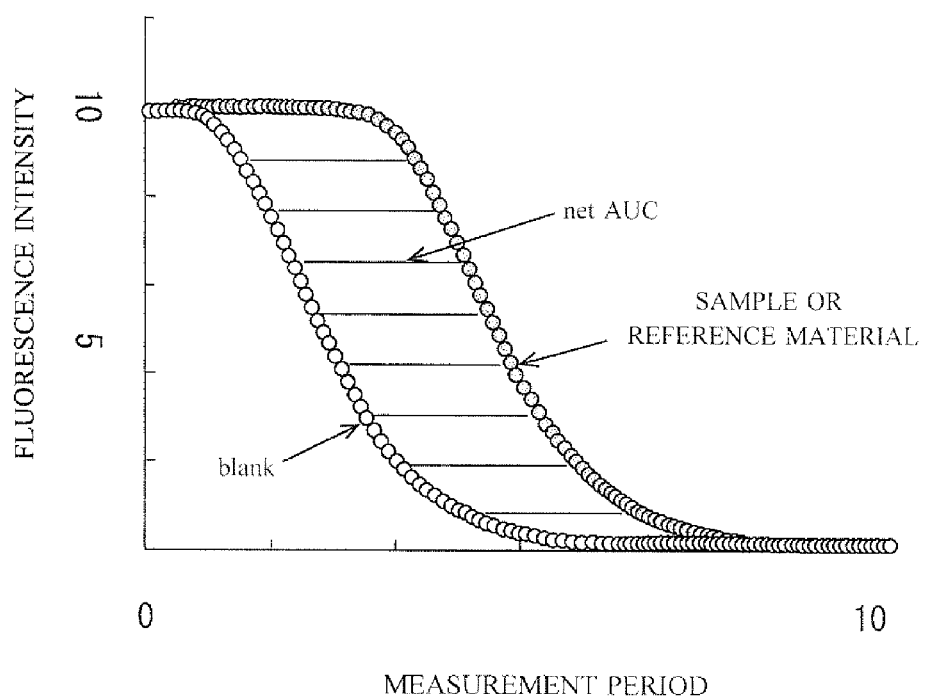
FIG. 9 is an explanatory view illustrating a measurement principle of an ORAC method.

Now, the measurement principle of the ORAC method will be somewhat described. First, in the case where constant reactive oxygen species are generated, the fluorescence intensity degraded by the reactive oxygen species is measured, and the curve of the fluorescence intensity decreasing over time is depicted, the rate of decrease in the fluorescence intensity of the fluorescent substance is delayed by coexistence of the antioxidant substance with the reaction system. Accordingly, with this principle, the presence of the antioxidant substance can be confirmed (see FIG. 9).

Figure 10:
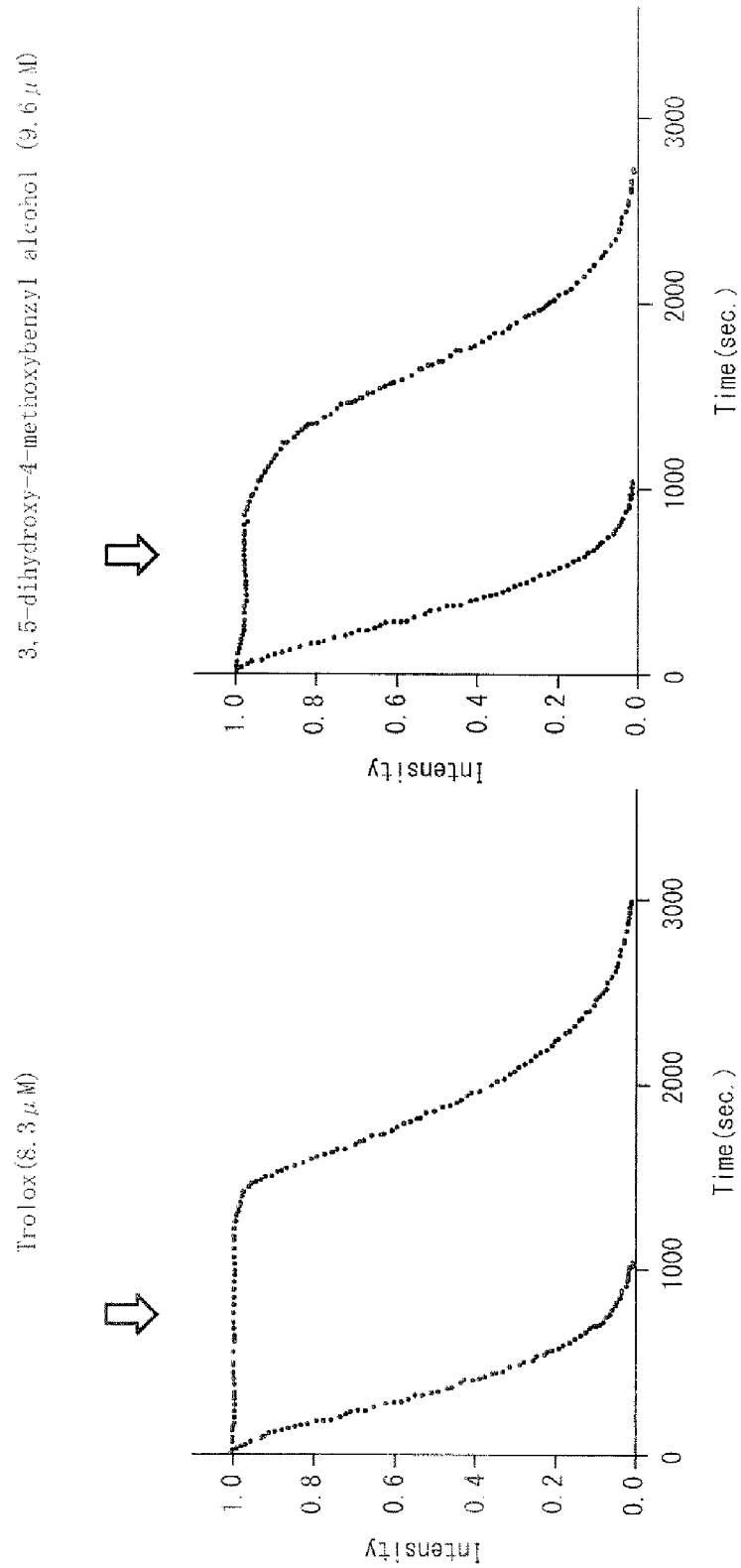
FIG. 10 is an explanatory view illustrating an antioxidant capacity of 3,5-dihydroxy-4-methoxybenzyl alcohol according to the present invention.

The antioxidant capacity of the 3,5-dihydroxy-4-methoxybenzyl alcohol according to the present invention was observed by the ORAC method. Then, a delay period was present, in the same manner as a reference material (Trolox), and high antioxidant activity was observed (see FIG. 10). In the present working example, the ORAC method was employed for investigation of the above-described supernatant 8. Accordingly, 3,5-dihydroxy-4-methoxybenzyl alcohol featuring high antioxidative potency was found in the ethyl acetate fraction.

Next, in both oxidation experiments of cultured hepatocyte and a low-density lipoprotein (LDL), the antioxidant activity of the 3,5-dihydroxy-4-methoxybenzyl alcohol is revealed.

(Antioxidant Activity of the Substance to the Metal Oxidation of Normal Human LDL)

Figure 11:
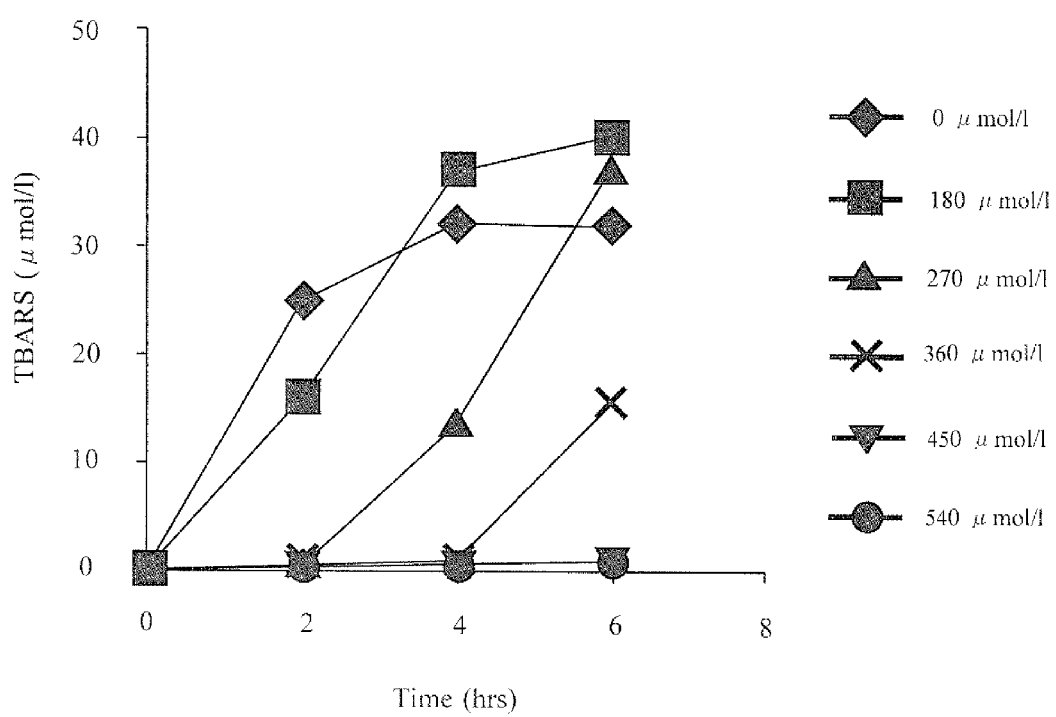
FIG. 11 is an explanatory view illustrating a state where a degree of oxidation of LDL is quantitated by a TBARS method.

When normal human LDL is oxidized by copper sulfate, 3,5-dihydroxy-4-methoxybenzyl alcohol was added, and the degree of oxidation of the LDL was quantitated by a TBARS method (see FIG. 11). When the substance was added at 180 μM, similarly to Control (0 μM), lag-time was not observed. The Lag-time refers to a period where a rise of a curve is not observed. It is determined that, as the time increases, antioxidant activity occurs. However, the lag-time was extended by dose dependency. The lag-time was 2 hours for addition of 270 μM, 4 hours for addition of 360 μM, and 5 hours for addition of 450 μM and 540 μM. It was confirmed that the 3,5-dihydroxy-4-methoxybenzyl alcohol reduced the metal oxidation of the LDL.

(Observation of an Antioxidant Capacity Using a Hepatocyte Culture System)

Figure 12:
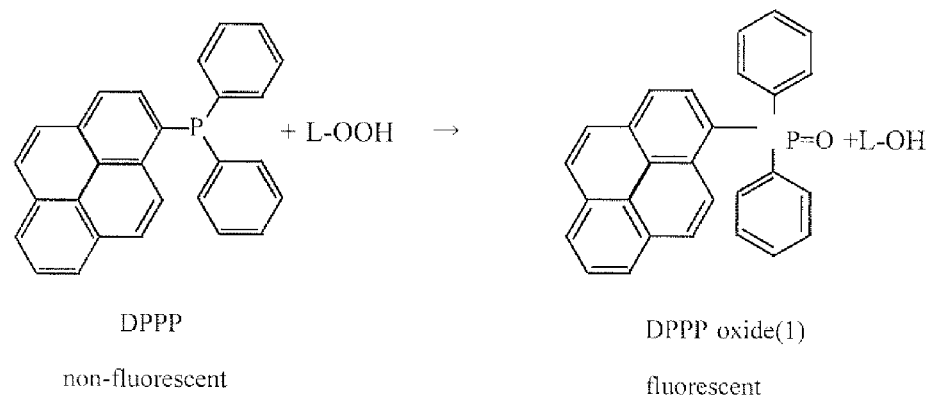
FIG. 12 is an explanatory view illustrating a principle of a fluorescence of diphenyl-1-pyrenlphosphine (DPPP)

Diphenyl-1-pyrenlphosphine (DPPP) does not generate a fluorescent light itself, but generates a fluorescent light by oxidation. FIG. 12 illustrates the principle of the fluorescence of the diphenyl-1-pyrenlphosphine (DPPP). Using the fluorescent dye, the degree of oxidation of a cell line (C3A) in a liver was observed.

Figure 13:
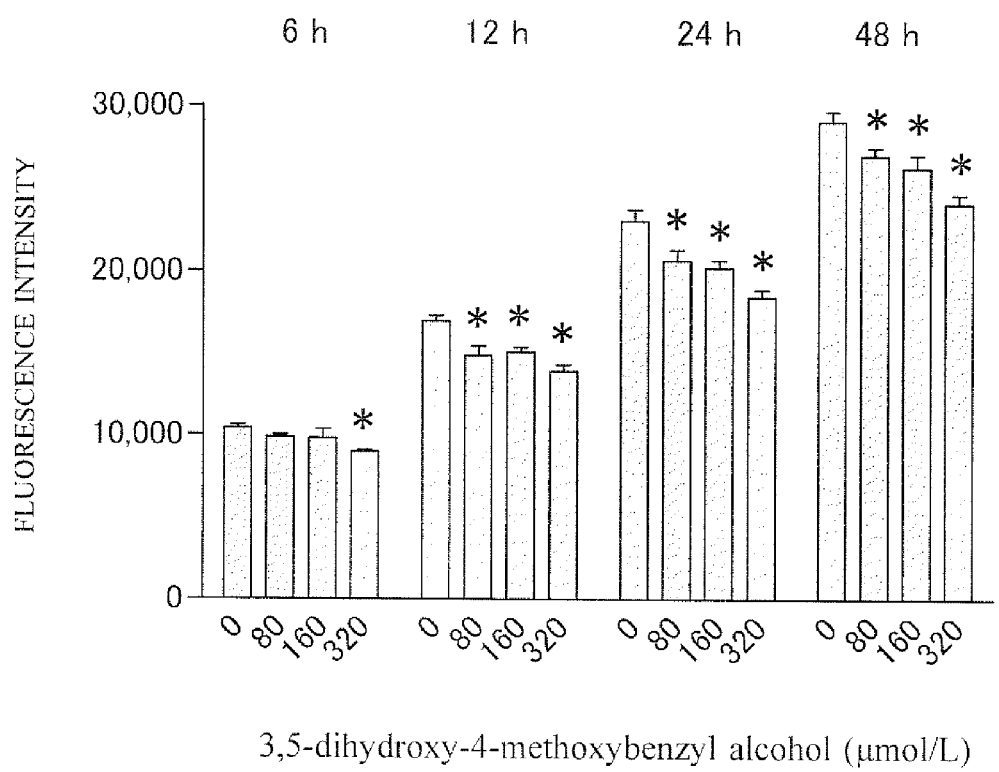
FIG. 13 is an explanatory view illustrating a state of oxidation inhibition by a cell where 3,5-dihydroxy-4-methoxybenzyl alcohol is doped according to the present invention.

A cell where the 3,5-dihydroxy-4-methoxybenzyl alcohol according to the present invention had been added was cultured for 5 days. The cell labeled by DPPP was oxidized by 2,2'-azobis (2-methylpropionamidine)dihydrochloide, and then the fluorescence intensity of the DPPP in each cell was measured. As a result, compared with the cell where 3,5-dihydroxy-4-methoxybenzyl alcohol was not added, the added cell exhibited concentration dependence and low fluorescence intensity. It was confirmed that the antioxidant substance, 3,5-dihydroxy-4-methoxybenzyl alcohol, reduced the oxidation (see FIG. 13).

As described above, it was apparent that 3,5-dihydroxy-4-methoxybenzyl alcohol featured an antioxidative property. The 3,5-dihydroxy-4-methoxybenzyl alcohol can be extracted from an oyster meat extract efficiently according to the present invention. Accordingly, a large amount of an antioxidant composition and an antioxidant can be recovered from the oyster meat extract and produced efficiently.

To confirm the constitution of 3,5-dihydroxy-4-methoxybenzyl alcohol, the inventors of the present invention conducted a chemosynthesis of 3,5-dihydroxy-4-methoxybenzyl alcohol, and have succeeded the chemosynthesis.

Figure 16:
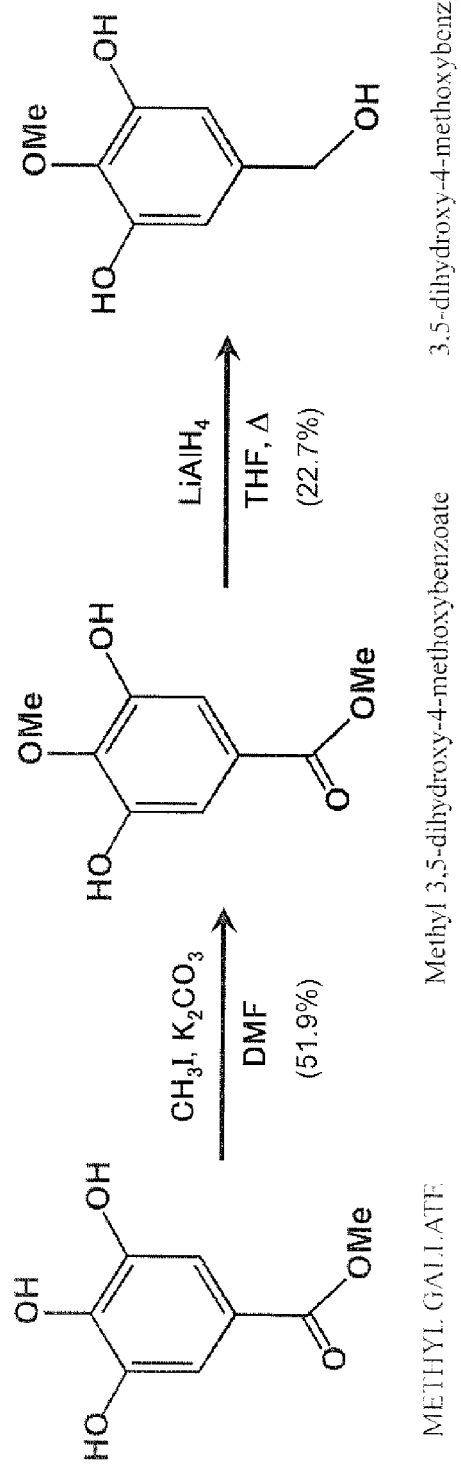
FIG. 16 is an explanatory view illustrating a chemosynthesis of 3,5-dihydroxy-4-methoxybenzyl alcohol.

FIG. 16 illustrates all steps of the chemosynthesis. The nuclear magnetic resonance spectrum (NMR: AMX-500, Bruker, Karlsruhe) and the mass spectrum (LXQ, Thermo-Scientific, Waltham) of the synthesized substance were measured to confirm the constitution. First, potassium carbonate (4.50 g, 32.6 mmol) was added to a dimethylformamide (DMF) solution (45 mL) with a methyl gallate (5.00 g, 27.2 mmol), and the solution was stirred for one hour at 85° C. Then, methyl iodide (4.00 g, 28.2 mmol) was gradually dropped and stirred for 30 minutes in an ice bath, and further stirred for 24 hours at room temperature. Reaction liquid was filtered, purified water was added, and extraction was performed with ethyl acetate. The separated ethyl acetate layer was washed with saturated saline and dehydrated by sodium sulfate.

After concentration, the extract liquid was purified by silica gel column chromatography (solvent: chloroform→chloroform-ethyl acetate (3:1, v/v)) and obtained 4-methoxy form of 2.79 g (yield: 51.9%).

Condition $^1$H-NMR (500 MHz, CD$_3$OD) $\delta_H$: 7.01 (2H, s, H-2, 6), 3.85 (3H, s, —OMe), 3.82 (3H, s, —OMe); $^{13}$C-NMR (125 MHz, CD$_3$OD) $\delta_C$: 168.5 (—C=O), 151.7 (C-3, 5), 141.2 (C-1), 126.5 (C-4), 110.1 (C-2, 6), 60.7 (—OMe), 52.5 (—OMe); ESI-ITMS, m/z199 [M+H]$^+$, 197[M−H]$^−$.

Next, a tetrahydrofuran solution (4 mL) with 4-methoxy form (560 mg, 2.8 mmol) with methyl gallate was dropped carefully to a tetrahydrofuran (THF) solution (6 mL) with lithium aluminum hydride (469 mg, 12.4 mmol) in an ice bath (0° C.). Then, the mixture was stirred for six hours at 60 to 65° C., ethyl acetate and a 10% sulfuric acid aqueous solution were added to the mixture, and then the reaction was stopped. Purified water was added to the reaction liquid, extraction was performed with the ethyl acetate, and the separated ethyl acetate layer was washed with saturated saline and dehydrated by sodium sulfate. After concentration, the extract liquid was purified by silica gel column chromatography (solvent: chloroform-methanol (50:1, v/v)→chloroform-methanol (50:3 , v/v)) and a reductant, that is, synthetic 3,5-dihydroxy-4-methoxybenzyl alcohol of 175.9 mg (yield: 36.6%) was obtained.

Condition $^1$H-NMR (500 MHz, Acetone-d$_6$) $\delta_H$: 7.82 (2H, br.s, aromatic-OH), 6.40 (2H, s, H-2, 6), 4.42 (2H, s, H-1'), 3.94 (1H, br.s, —OH), 3.79 (3H, s, —OMe); $^{13}$C-NMR (125 MHz, Acetone-d$_6$) $\delta_C$: 151.1 (C-3, 5), 139.4 (C-1), 13, 5.1 (C-4), 106.5 (C-2, 6), 64.5 (C-1'), 60.6 (—OMe); ESI-ITMS, m/z171 [M+H]$^+$, 153[M-OH]$^+$.

(Comparison Between 3,5-dihydroxy-4-methoxybenzyl Alcohol and the Physical Parameter of the Synthetic Compound)

Between 3,5-dihydroxy-4-methoxybenzyl alcohol and the synthetic compound, various spectral data of the above-described $^1$H-NMR, $^{13}$C-NMR, and ESI-MS coincided and the duration of HPLC and the mobility of a Thin-Layer-Chromatography coincide. It was confirmed that 3,5-dihydroxy-4-methoxybenzyl alcohol existed in the synthetic compound.

As described above, 3,5-dihydroxy-4-methoxybenzyl alcohol, which is the antioxidant substance obtained from the oyster, can be said to have a highly hydroxylated aromatic compound. Up to now, it has been reported that a hydroxylated aromatic, namely, phenolic compounds include many substances featuring antioxidant activity, such as chlorogenic acid represented by caffeic acid, nigrin group, and flavonoid.

It is known that these substances produce antioxidant activity by serving as a capture agent for peroxide, especially, peroxy radical (ROO.). Accordingly, the antioxidant substance identified in the present invention exhibited high antioxidant activity in ORAC where radical scavenging ability was observed and in cell experiments using AAPH. This strongly suggests the possibility that the substance can produce an antioxidant capacity serving as a radical scavenger.

The substance purified according to the present invention features an amphipathic nature. However, the substance had an ORAC value three times of that of L(+)-ascorbic acid, which is broadly used as one of the few water-soluble antioxidants. Accordingly, there are high expectations for the effect of the substance as an antioxidant. Reduction of oxidation of the LDL by the substance in a dose-dependent manner suggests an effect that the substance produces an anti-atherogenic action through preventing oxidation of the LDL.

On the other hand, to observe oxidation of a living cell in real-time, a probe such as cis-parinaricacid (PnA), fluoresceinatedphosphoethanolamine, and undecylamine-fluorescein have been developed. Among them, PnA is frequently used as a probe for observing oxidation of a living cell. However, it is reported that PnA often exhibits cytotoxicity and affects physiological activity of a cell.

The DPPP used in the present invention did not affect cell proliferation, cytotoxicity, or similar reaction for at least three days. It has been reported that the DPPP and the oxidized DPPP localized at the cell membrane of the living cell were stable for at least two days. The DPPP does not generate a fluorescent light itself, but the oxidized DPPP generates a fluorescent light. Using the DPPP, conventionally, a method for observing a lipid peroxide of a living cell has been established. Antioxidative potency of a vitamin E was confirmed using human monocytic lineage cells (U937) in suspension.

In the present invention, the antioxidant substance significantly reduced oxidation of a C3A cell, which is a cell line derived from a liver. This suggests that the substance according to the present invention can produce antioxidant activity at least even in a hepatocyte. With this result together with the above-described reduction of LDL oxidation, there are high expectations about the effect of the substance as an antioxidant.

As diseases associated with oxidant stress, conventionally, arteriosclerotic disease has generated much interest. In recent years, an ectopic fat storage disease such as a non-alcoholic steatohepatitis (NASH) has been drawing attention. In NASH, it is known that reactive oxygen relates to a hepatocellular necrosis, inflammatory cytokine production, and liver fibrosis. In NASH, it is reported that an oxidized LDL concentration is high in the blood. Furthermore, it is reported that an increase in the inflammatory cytokine production in NASH and a hepatic stellate cell involved in an increase in collagen production are activated by the oxidized LDL. Novel antioxidant substances from oysters found in the present invention can be highly expected to contribute to prevention of NASH.

Thus, the present invention has found a novel antioxidant substance from an oyster and has determined the chemical constitution as 3,5-dihydroxy-4-methoxybenzyl alcohol. Further, the chemosynthesis method has also been determined. Furthermore, the ORAC value of the substance according to the present invention is 1.24±0.3, 5 μmolTE/μmol in the purified product and 1.47±0.40 μmolTE/μmol in the synthesized product. The substance showed a high antioxidant capacity between those of a chlorogenic acid and L(+)- the ascorbic acid of a water-soluble antioxidant.

The substance according to the present invention, 3,5-dihydroxy-4-methoxybenzyl alcohol, showed an antioxidant capacity in a dose-dependent manner to metal oxidation of human LDL. Also, in the antioxidant capacity experiment using a C3A cell, the substance showed an antioxidant capacity in a dose-dependent manner.

LIST OF REFERENCE SYMBOLS 1 extraction container
2 extraction solution
3 raw oyster meat
4 ethanol solution
5 ethyl acetate
6 concentrated liquid
7 precipitate
8 supernatant
9 concentrated liquid of supernatant
10 diluted solution

The invention claimed is:

1. A method for producing an antioxidant composition, comprising:

(1) adding an oyster meat to an extraction container containing water to obtain an extract liquid containing an oyster meat extract;
(2) concentrating the extract liquid;
(3) adding liquid ethanol to the concentrated extract liquid to achieve an ethanol concentration of 70%, then stirring a resulting liquid;
(4) after stirring, the liquid of step (3) is allowed to rest to separate a precipitate and a supernatant;
(5) removing the ethanol from the supernatant;
(6) concentrating the supernatant resulting from step (5) until an amount of the solution is half that of step (5);
(7) diluting the concentrated liquid of step (6) so as to quintuple the amount of the concentrated liquid of step (6) to remove impurities;
(8) adding ethyl acetate to the liquid of step (7) to achieve a solution;
(9) separating the solution of step (8) into a water layer and an ethyl acetate layer with a separator; and
(10) recovering a 3,5-dihydroxy-4-methoxybenzyl alcohol fraction from the ethyl acetate layer.

2. A method for producing an antioxidant composition, comprising
(1) adding an oyster meat to an extraction container containing water and liquid ethanol to obtain an extract liquid containing an oyster meat extract;
(2) concentrating the extract liquid;
(3) adding liquid ethanol to the concentrated extract liquid to achieve an ethanol concentration of 70%, then stirring a resulting liquid;
(4) after stirring, the liquid of step (3) is allowed to rest to separate a precipitate and a supernatant;
(5) removing the ethanol from the supernatant;
(6) concentrating the supernatant resulting from step (5) until an amount of the solution is half that of step (5);
(7) diluting the concentrated liquid of step (6) so as to quintuple the amount of the concentrated liquid of step (6) to remove impurities;
(8) adding ethyl acetate to the liquid of step (7) to achieve a solution;
(9) separating the solution of step (8) into a water layer and an ethyl acetate layer with a separator; and
(10) recovering a 3,5-dihydroxy-4-methoxybenzyl alcohol fraction from the ethyl acetate layer.

3. A method for producing an antioxidant composition, comprising:
(1) storing an oyster meat in an extraction container where an extraction solution is accumulated;
(2) collecting a solution with an oyster meat extract from the extraction container;
(3) adding ethyl acetate to the collected solution with an oyster meat extract;
(4) separating the solution of step (3) into a water layer and an ethyl acetate layer with a separator; and
(5) recovering a 3,5-dihydroxy-4-methoxybenzyl alcohol fraction from the ethyl acetate layer.

4. A method for producing an antioxidant composition, comprising:
(1) storing an oyster meat in an extraction container where an extraction solution is accumulated;
(2) collecting a solution with an oyster meat extract from the extraction container;
(3) adding ethyl acetate and ethanol to the collected solution with an oyster meat extract, then stirring a resulting liquid;
(4) after stirring, the liquid of step (3) is allowed to rest to separate a precipitate and a supernatant;
(5) removing the ethanol from the supernatant;
(6) concentrating the supernatant resulting from step (5) until an amount of the solution is half that of step (5);
(7) diluting the concentrated liquid of step (6) so as to quintuple the amount of the concentrated liquid of step (6) to remove impurities;
(8) adding ethyl acetate to the liquid of step (7) to achieve a solution;
(9) separating the solution of step (8) into a water layer and an ethyl acetate layer with a separator; and
(10) recovering a 3,5-dihydroxy-4-methoxybenzyl alcohol fraction from the ethyl acetate layer.

5. A method for producing an antioxidant composition, comprising:
(1) storing an oyster meat in an extraction container where an extraction solution is accumulated;
(2) collecting a solution with an oyster meat extract from the extraction container;
(3) adding ethanol to the collected solution with an oyster meat extract to separate the solution into a supernatant and a precipitate;
(4) removing the separated supernatant;
(5) removing the ethanol from the supernatant;
(6) adding ethyl acetate to the supernatant of step (5) to separate the solution into an ethyl acetate layer and a water layer;
(7) concentrating a solution of the separated ethyl acetate layer; and
(8) recovering a 3,5-dihydroxy-4-methoxybenzyl alcohol fraction from the ethyl acetate layer.

* * * * *